(12) United States Patent
Arai

(10) Patent No.: US 7,354,891 B2
(45) Date of Patent: Apr. 8, 2008

(54) PEARLESCENT DETERGENT COMPOSITION COMPRISING A MIXTURE OF ETHYLENE GLYCOL ALKYLATES

(75) Inventor: Kenji Arai, Tokyo (JP)

(73) Assignee: Kao Corporation, Tokyo (JP)

( * ) Notice: Subject to any disclaimer, the term of this patent is extended or adjusted under 35 U.S.C. 154(b) by 24 days.

(21) Appl. No.: 10/523,395

(22) PCT Filed: Aug. 8, 2003

(86) PCT No.: PCT/JP03/10137

§ 371 (c)(1),
(2), (4) Date: Feb. 3, 2005

(87) PCT Pub. No.: WO2004/015048

PCT Pub. Date: Feb. 19, 2004

(65) Prior Publication Data

US 2006/0046942 A1    Mar. 2, 2006

(30) Foreign Application Priority Data

Aug. 9, 2002    (JP) .............................. 2002-232735

(51) Int. Cl.
*C11D 9/44* (2006.01)
(52) U.S. Cl. ...................... 510/416; 510/119; 510/130; 510/146; 510/441; 510/437; 510/438; 510/444
(58) Field of Classification Search ................ 510/119, 510/130, 146, 441, 437, 438, 416, 444
See application file for complete search history.

(56) References Cited

U.S. PATENT DOCUMENTS

| 4,486,334 | A  | * | 12/1984 | Horiuchi et al. ............... 516/77 |
| 5,545,354 | A  | * | 8/1996  | Ofosu-Asante ............. 510/237 |
| 6,165,955 | A  | * | 12/2000 | Chen et al. .................. 510/123 |
| 6,210,659 | B1 | * | 4/2001  | Wilhelm et al. ......... 424/70.24 |
| 6,294,160 | B1 | * | 9/2001  | Decoster .................. 424/70.19 |
| 6,417,146 | B1 | * | 7/2002  | Miyajima et al. ........... 510/130 |

FOREIGN PATENT DOCUMENTS

| JP | 56-133400  | 10/1981 |
| JP | 7-258699   | 10/1995 |
| JP | 8-231985   | 9/1996  |
| JP | 9-111291   | 4/1997  |
| JP | 2002-20790 | 1/2002  |
| JP | 2002-121131| 4/2002  |

* cited by examiner

*Primary Examiner*—Charles Boyer
(74) *Attorney, Agent, or Firm*—Oblon, Spivak, McClelland, Maier & Neustadt, P.C.

(57) ABSTRACT

A process for preparing—a cleansing composition having pearlescence, which contains adding an ingredient (B) which has been molten beforehand, or an aqueous liquid in which the molten ingredient (B) is contained, to a suspension of an ingredient (A) and cooling the resultant mixture to cause the ingredient (B) to deposit; and the cleansing composition.

The process makes it possible to economically produce cleansing compositions which have pearlescence, excellent in the stability of their pearlants, and superb long-term storage stability under acidic conditions and high-temperature conditions.

20 Claims, No Drawings

PEARLESCENT DETERGENT COMPOSITION COMPRISING A MIXTURE OF ETHYLENE GLYCOL ALKYLATES

FIELD OF THE INVENTION

This invention relates to cleansing compositions having pearlescence and a process for preparing them, and specifically to cleansing compositions which are excellent in the stability of their pearlants, are superb in long-term storage stability under acidic conditions and high-temperature conditions, are inexpensive, and a production process thereof.

BACKGROUND OF THE INVENTION

Cleansing compositions have been developed with a view to achieving both an improved cleansing function and providing a mild feel and conditioning effects. As the life style diversifies, however, the consumers' demand has also been diversified, resulting in the demand for an expanded availability with respect to the external appearance and function of cleansing compositions.

Concerning the external appearance of cleansing compositions, the impartation of a pearly appearance can give a luxurious impression, and thus make consumers feel rich. As to the function of cleansing compositions, there is a demand not only for cleansing performance but also for a wide variety of functions such as the impartation of a silky feel, manageability, combing ease and the like to the hair in the case of hair cleansing compositions, for example.

To impart a pearly appearance, the use of alkylene glycol mono- or dialkylates has been known conventionally. They, however, have such a broad distribution in their alkyl chain length due to their raw materials that an intended pearly appearance can hardly be achieved. For the impartation of a silky feel, manageability, combing ease and the like, it is known to make the pH of a cleansing composition acidic. The acidification of the pH of the composition, however, involves problems that its pearlant in the form of an ester undergoes decomposition and the stability of the composition is considerably deteriorated, specifically, the composition loses its uniformity and its pearly appearance is impaired.

DISCLOSURE OF THE INVENTION

This invention provides a process for preparing a cleansing composition having pearlescence and also the cleansing composition. The process contains mixing an aqueous liquid in which the following ingredient (A) is suspended with the following ingredient (B) which has been molten beforehand, or an aqueous liquid in which the molten ingredient (B) is contained, and cooling the resultant mixture to cause the ingredient (B) to deposit:

Ingredient (A): an ester ingredient consisting of an ethylene glycol monoalkylate or ethylene glycol dialkylate which may have a distribution in the number of carbon atoms in its constituent fatty acid with a proviso that fatty acids having carbon numbers of 18 and greater account for less than 70 wt. % of all constituent fatty acids; and Ingredient (B): an ester ingredient consisting of an ethylene glycol monoalkylate or ethylene glycol dialkylate which may have a distribution in the number of carbon atoms in its constituent fatty acid with a proviso that fatty acids having carbon numbers of 18 and greater account for 70 wt. % or more of all constituent fatty acids.

BEST MODES FOR CARRYING OUT THE INVENTION

This invention relates to a cleansing composition which is acidic, is excellent in the stability of its pearlant and has pearlescence, and also to a process thereof.

The present inventors have found that a cleansing composition, which has a superb external appearance and is excellent in the stability of its pearlant under acidic condition, can be economically produced by using a commonly-used pearlant in combination with an ethylene glycol alkylate whose distributions in the number of carbon atoms of its constituent fatty acids fall within a specific range, and by causing crystals of the latter to deposit in a system in which crystals of the former are suspended.

Ingredients (A) and (B) useful as pearlants in the present invention are both ethylene glycol monoalkylates or ethylene glycol dialkylates. Ingredient (A) is a pearlant which is widely marketed and used. Ingredient (B), on the other hand, is characterized in that the percentage of ester-constituting fatty acids having greater carbon numbers is higher compared with general pearlants.

For ingredient (B), fatty acids having carbon numbers of 18 and greater account for 70 wt. % or more of all constituent fatty acids, with 80 wt. % or more being preferred from the standpoint of stability under acidic condition. The carbon numbers of the fatty acids which account for 70 wt. % or more of all the constituent fatty acids can preferably fall within a range of from 18 to 22. Further, the distribution in the number of carbon atoms in all the fatty acids can preferably fall within a range of from 11 to 22.

When fatty acids having 18 and greater carbon numbers account for 70 to 85 wt. % of all the fatty acids in the combination of ingredients (A) and (B), the resulting cleansing composition is provided with excellent lathering ability, pearly appearance and stability.

The content of ingredient (A) or (B) in "the aqueous liquid in which the ingredient (A) is suspended" or in "the aqueous liquid which contains the molten ingredient (B)" can be preferably from 0.1 to 50 wt. %, more preferably from 0.5 to 40 wt. % from the standpoint of stability and external appearance. The weight ratio of ingredient (A) to ingredient (B) to be used can be preferably in a range of $0.1 < (A)/[(A)+(B)] < 0.9$, more preferably in a range of $0.3 < (A)/[(A)+(B)] < 0.7$ from the standpoint of stability and external appearance.

"The aqueous liquid in which the ingredient (A) is suspended" or "the aqueous liquid which contains the molten ingredient (B)" may contain a surfactant as a dispersant. As such a surfactant, an anionic surfactant or amphoteric surfactant can be mentioned.

As anionic surfactants, sulfate-type anionic surfactants, sulfonate-type anionic surfactants and carboxylate-type anionic surfactant are preferred. Examples include alkyl sulfates, polyoxyalkylene alkyl ether sulfates, polyoxyalkylene alkenyl ether sulfates, sulfosuccinate alkylene alkylphenyl ether sulfates, and higher fatty acid salts. Among these, preferred are polyoxyalkylene alkyl ether sulfates, polyoxyalkylene alkenyl ether sulfates and alkyl sulfates, with those represented by the following formula (1) or (2) being preferred.

(1)

(2)

wherein $R^1$ represents an alkyl or alkenyl group having a carbon number of from 10 to 18, $R^2$ represents an alkyl group having a carbon number of from 10 to 18, M represents an alkali metal, alkaline earth metal, ammonium, alkanolamine or basic amino acid, and m stands for the value of from 1 to 5 on weight average.

As amphoteric surfactants, acetobetaine-type amphoteric surfactants, amidoacetobetaine-type amphoteric surfactants, sulfobetaine-type amphoteric surfactants, amidosulfobetaine-type amphoteric surfactants, phosphobetaine-type amphoteric surfactants, alkylamine oxides, amidoamine oxides and the like can be mentioned. Among these, fatty acid amidopropyl betaines such as coconut oil fatty acid amidopropyl betaine and lauramidopropyl betaine are preferred.

Two or more of these surfactants may be used in combination. The content of such a surfactant in "the aqueous liquid in which the ingredient (A) is suspended" or in "the aqueous liquid which contains the molten ingredient (B)" can preferably be from 1 to 70 wt. %, more preferably from 5 to 50 wt. %, even more preferably from 7 to 30 wt. %.

In the aqueous liquids, a water-soluble high molecular substance may be incorporated to improve the dispersion stability. As the water-soluble high molecular substance, a cationic polymer or nonionic polymer is preferred, with cationized cellulose or cationized guar gum being preferred.

The cleansing composition according to the present invention can be produced by adding the ingredient (B) which has been molten beforehand, or the aqueous liquid which contains the molten ingredient (B), to the aqueous liquid in which the ingredient (A) is suspended, and cooling the resultant mixture to cause the ingredient (B) to deposit.

The aqueous liquid in which the ingredient (A) is suspended can be produced in accordance with a usual process for the production of pearly suspensions. Described specifically, the ingredient (A), water and, if necessary, a surfactant and/or water-soluble high molecular substance are mixed, heated, and stirred. The heating temperature can be set above the melting point of ingredient (A), preferably at a temperature higher by 10° C. or more of the melting point of ingredient (A). The stirring speed can preferably be from 10 to 100 rpm, and from the standpoint of working efficiency, the stirring time can preferably be from 5 to 60 minutes. As a result, the ingredient (A) is molten and the liquid is brought into an emulsified, dispersed state. With stirring, the liquid is then gradually cooled and is kept at room temperature such that the ingredient (A) is caused to deposit.

Ingredient (B) to be added to the suspension of ingredient (A) is required to being molten state. The molten ingredient (B) can be added by itself, or an aqueous liquid in which the molten ingredient (B) is contained can be added. The aqueous liquid in which the molten ingredient (B) is contained can be prepared in a similar manner as in the above-described ingredient (A). Described specifically, the ingredient (B), water and, if necessary, a surfactant and/or water-soluble high molecular substance are mixed, heated, and stirred. The heating temperature can be set above the melting point of ingredient (B), preferably at a temperature higher by 10° C. or more of the melting point of ingredient (B). The stirring speed can preferably be from 10 to 100 rpm, and from the standpoint of working efficiency, the stirring time can preferably be from 5 to 60 minutes. As a result, the ingredient (B) is molten and the liquid is brought into an emulsified, dispersed state.

When the molten ingredient (B) or the aqueous liquid containing the molten ingredient (B) is added to the suspension of ingredient (A) and the resultant mixture is cooled, the ingredient (B) deposits on the surfaces of the crystals of ingredient (A) so that the cleansing composition having pearlescence according to the present invention can be obtained.

As an alternative, the addition of the molten ingredient (B) or the aqueous liquid which contains the molten ingredient (B) to the suspension of the ingredient (A) can also be effected by successively adding the suspension of ingredient (A) and ingredient (B) or the aqueous liquid which contains the ingredient (B) to an aqueous solution which has been prepared separately to contain an anionic surfactant, amphoteric surfactant, cationic surfactant or the like.

The cleansing composition having pearlescence, which has been prepared as described above, is stably dispersed under acidic condition and is excellent especially in high-temperature stability, and can be suitably used especially as a cleansing composition such as a shampoo, body wash or facial wash.

The total content of ingredients (A) and (B) in the cleansing composition according to the present invention may preferably be from 0.3 to 10 wt. %, more preferably from 0.5 to 5 wt. %, even more preferably from 0.8 to 3 wt. % from the viewpoint of beautiful pearlescence and good stability (especially, stability at high temperatures).

The cleaning composition according to the present invention can have a pH of preferably from 1 to 5, especially from 3 to 4 as measured in the form of a 5 wt. % aqueous solution [20-fold dilute solution (by weight)] at 25° C. For the adjustment of the pH, an organic acid or inorganic acid can be used. Examples of the organic acid include hydroxy acids, monocarboxylic acids, dicarboxylic acids, tricarboxylic acids, polycarboxylic acids, alkyl sulfates, and alkyl phosphates. Examples of the hydroxy acid include glycolic acid, lactic acid, oxybutyric acid, glyceric acid, malic acid, and tartaric acid. Examples of the monocarboxylic acid include acetic acid, examples of the dicarboxylic acid include malonic acid, succinic acid, glutamic acid, adipic acid, maleic acid, fumaric acid and phthalic acid, and examples of the tricarboxylic acid include citric acid. Examples of the inorganic acid include hydrochloric acid, sulfuric acid, and phosphoric acid. Among these, organic acids are preferred, and α-hydroxycarboxylic acids, especially lactic acid and malic acid are superior in providing sleekness, softness, flexibility and manageability to the hair. The content of an organic acid or inorganic acid in the cleansing composition according to the present invention can be preferably from 0.05 to 10 wt. %, more preferably from 0.1 to 5 wt. %, even more preferably from 0.5 to 1 wt. %.

In the cleansing composition according to the present invention, a silicone can be incorporated to further improve the conditioning effects. Examples of the silicone include dimethylpolysiloxane (viscosity: 5 to $2 \times 10^7$ mm$^2$/s), amino-modified silicones, polyether-modified silicones, methylphenylpolysiloxane, fatty-acid-modified silicones, alcohol-modified silicones, alkoxy-modified silicones, epoxy-modified silicones, fluorine-modified silicones, cyclic silicones, and alkyl-modified silicones, with dimethylpolysiloxane being more preferred. The content of the silicone in the cleansing composition according to the present invention can preferably be from 0.01 to 10 wt. %.

In the cleansing composition according to the present invention, one or more other conditioning ingredient(s) such as cationic polymers (cationized cellulose, cationized guar gum, and the like) can be incorporated. The content of such other conditioning ingredient(s) in the cleansing composition according to the present invention can preferably be from 0.1 to 5 wt. %.

In addition to the above-described ingredients, ingredients which are employed in ordinary cleansing and cosmetic compositions can also be incorporated in the cleansing composition according to the present invention as needed depending upon the purpose of use. Such ingredients can include humectants such as propylene glycol, glycerin, diethylene glycol monoethyl ether, sorbitol and panthenol; colorants such as dyes and pigments; viscosity controlling agents such as methylcellulose, polyethylene glycol and ethanol; and further, plant extracts, preservatives, antifungal and/or antimicrobial agents, chelating agents, vitamins, anti-inflammatories, fragrances, ultraviolet absorbers, antioxidants, and the like.

The cleansing composition according to the present invention is very useful as a hair cleansing composition, skin cleansing composition or the like.

EXAMPLES

Example 1

(1) Preparation of a Suspension of the Ingredient (A)

Water (10 g), ethylene glycol dialkylate [ingredient (A): acyl group (carbon number: 18) ester, 50 wt. %; acyl group (carbon number: 16) ester, 50 wt. %; 20 g], a 30 wt. % aqueous solution (67 g) of sodium polyoxyethylene lauryl sulfate and coconut oil fatty acid monoethanolamide (3 g) were heated to 80° C. and then stirred for about 1 hour to give a homogeneously-emulsified dispersion. Under gentle stirring, the dispersion was then allowed to gradually cool down to room temperature to give a solid suspension having an average particle size of not greater than 1,000 μm.

(2) Production of a Cleansing Composition (Shampoo) Having Pearlescence According to the Present Invention Water (40.5 g), a 30 wt. % aqueous solution (50 g) of sodium polyoxyethylene lauryl sulfate, coconut oil fatty acid monoethanolamide (2 g) and cationized cellulose (0.5 g) were heated to 80° C. and then stirred for about 1 hour to give a homogeneously-emulsified dispersion. Under gentle stirring, the dispersion was then allowed to gradually cool down. When the temperature dropped to around 57° C., the suspension (5 g) of the ingredient (A) obtained in the above-described procedure (1) was added. Added next at 56° C. was a melt (1 g) of ethylene glycol dialkylate heated at about 80° C. [ingredient (B): acyl group (carbon number: 18) ester, 95 wt. %; acyl group (carbon number: 16) ester, 5 wt. %]. The resultant mixture was allowed to gradually cool down to room temperature to give a shampoo according to the present invention. Subsequently, the pH of the composition [20-fold dilute solution (by weight)] was adjusted to 3.8 by using lactic acid (1 g) and hydrochloric acid or sodium hydroxide (q.s.).

Example 2

A shampoo according to the present invention [pH of 20-fold dilute solution (by weight): 3.8] was obtained in a similar manner as in the procedure (2) of Example 1 except that the amounts of water and the suspension of the ingredient (A) were changed to 38.5 g and 7 g, respectively, and in place of the cationized cellulose, the same amount of "MERQUAT 550" (product of Calgon Corp.) was used.

Example 3

A shampoo according to the present invention [pH of 20-fold dilute solution (by weight): 3.8] was obtained in a similar manner as in the procedure (2) of Example 1 except that the amounts of water, the suspension of the ingredient (A) and the melt of the ingredient (B) were changed to 41.5 g, 3 g and 2 g, respectively, and in place of the cationized cellulose, the same amount of cationized guar gum was used.

Example 4

A shampoo according to the present invention [pH of 20-fold dilute solution (by weight): 3.8] was obtained in a similar manner as in the procedure (2) of Example 1 except that the amount of water was changed to 39.5 g, and in place of the melt of the ingredient (B), a mixture (1:1 by weight; 2 g) of the ingredient (B) and propylene glycol which had been heated to 80° C. was used.

Comparative Example 1

Water (41 g), a 30 wt. % aqueous solution (46.65 g) of sodium polyoxyethylene lauryl sulfate, coconut oil fatty acid monoethanolamide (1.85 g) and cationized cellulose (0.5 g) were heated to 80° C. and then stirred for about 1 hour to give a homogeneous liquid. Under gentle stirring, the liquid was then allowed to gradually cool down. When the temperature dropped to around 57° C., the suspension (10 g) of the ingredient (A) obtained in the procedure (1) of Example 1 was added. The resultant mixture was then allowed to gradually cool down to room temperature to give a shampoo.

Test 1

The shampoos obtained in Examples 1-4 and Comparative Example 1 were ranked for the appearance, the touching feel of the foam and the stability under acidic condition in accordance with the following standards. The results are shown in Table 1.

Ranking Standards

External Appearance

The external appearance of each shampoo was visually observed, and was ranked in accordance with the following standard.

A: Strongly pearly appearance.
B: Lightly pearly appearance.
C: No pearly appearance.

Touching Feel of the Foam

Adequate amounts of each shampoo and water were taken on the hands and were then foamed. A touching feel at that time was ranked in accordance with the following standard.

A: Soft and silky.
B: Coarse and collapsed feel.

Stability Under Acidic Condition

Each shampoo was stored while maintaining its temperature at 50° C. A period of time during which the stability (pearly appearance) of the system was maintained was determined.

A: Remained stable for 1 month or longer.
B: Stable for 20 days.
C: Pearly appearance disappeared in less than 20 days.

TABLE 1

|  | Examples | | | | Comp. Ex. |
| --- | --- | --- | --- | --- | --- |
|  | 1 | 2 | 3 | 4 | 1 |
| External appearance | A | A | A | A | A |
| Touching feel of the foam | A | A | A | A | A |
| Stability under acidic condition | A | A | A | A | B |

The invention claimed is:

1. A process for preparing a cleansing composition having pearlescence, which comprises:
    mixing an aqueous liquid in which an ingredient (A) is suspended with an ingredient (B), which is molten prior to mixing, or an aqueous liquid in which said molten ingredient (B) is contained; and
    cooling the resultant mixture to cause said ingredient (B) to deposit on a surface of ingredient (A), wherein:
    said ingredient (A) is at least one ester selected from the group consisting of an ethylene glycol monoalkylate and ethylene glycol dialkylate, which may have a distribution in the number of carbon atoms in its constituent fatty acids, with the proviso that fatty acids having carbon numbers of 18 and greater account for less than 70 wt. % of all of said constituent fatty acids; and
    said ingredient (B) is at least one ester selected from the group consisting of an ethylene glycol monoalkylate and ethylene glycol dialkylate, which may have a distribution in the number of carbon atoms in its constituent fatty acids, with the proviso that fatty acids having carbon numbers of 18 and greater account for 70 wt. % or more of all of said constituent fatty acids wherein said cleansing composition exhibits a pearlescence stability of at least 1 month at 50° C. at a pH of 3.8.

2. The process according to claim 1, wherein the aqueous liquid in which said ingredient (A) is suspended and/or said aqueous liquid in which said molten ingredient (B) is contained further comprises a surfactant.

3. A cleansing composition having pearlescence, which is obtained by a method comprising:
    adding an ingredient (B), which is molten prior to mixing, or an aqueous liquid in which said molten ingredient (B) is contained, to an aqueous liquid in which an ingredient (A) is suspended; and
    cooling the resultant mixture to cause said ingredient (B) to deposit on a surface of ingredient (A),
    wherein: said ingredient (A) is at least one ester selected from the group consisting of an ethylene glycol monoalkylate and ethylene glycol dialkylate, which may have a distribution in the number of carbon atoms in its constituent fatty with the proviso that fatty acids having carbon numbers of 18 and greater account for less than 70 wt. % of all of said constituent fatty acids; and
    said ingredient (B) is at least one ester selected from the group consisting of an ethylene glycol monoalkylate and ethylene glycol dialkylate, which may have a distribution in the number of carbon atoms in its constituent fatty acids with the proviso that fatty acids having carbon numbers of 18 and greater account for 70 wt. % or more of all of said constituent fatty acids wherein said cleansing composition exhibits a pearlescence stability of at least 1 month at 50° C. at a pH of 3.8.

4. The cleansing composition according to claim 3, wherein said aqueous liquid in which said ingredient (A) is suspended and/or said aqueous liquid in which said molten ingredient (B) is contained further comprises a surfactant.

5. The process of claim 1, wherein for ingredient (B), fatty acids having carbon numbers of 18 and greater account for 80 wt. % or more of all of said constituent fatty acids.

6. The process of claim 1, wherein the carbon number of the fatty acids which account for 70 wt. % or more of all the constituent fatty acids fall within a range of from 18 to 22.

7. The process of claim 1, wherein fatty acids having 18 and greater carbon numbers account for 70 to 85 wt. % of all the fatty acids in the combination of ingredients (A) and (B).

8. The process of claim 1 where the weight ratio of ingredient (A) to ingredient (B) is in a range of 0.1<(A)/[(A)+(B)]<0.9.

9. The process of claim 2, wherein said surfactant is present in an amount of 1 to 70 wt. %.

10. The process of claim 1, wherein a total content of ingredients (A) and (B) in said cleansing composition is 0.3 to 10 wt. %.

11. The process of claim 1, wherein said cleaning composition has a pH of from 3 to 4.

12. The process of claim 1, wherein a content of ingredient (A) or (B) in said aqueous liquid in which the ingredient (A) is suspended or in said aqueous liquid which contains said molten ingredient (B) is 0.1 to 50 wt. %.

13. The cleansing composition of claim 3, wherein for ingredient (B), fatty acids having carbon numbers of 18 and greater account for 80 wt. % or more of all of said constituent fatty acids.

14. The cleansing composition of claim 3, wherein the carbon number of the fatty acids which account for 70 wt. % or more of all the constituent fatty acids fall within a range of from 18 to 22.

15. The cleansing composition of claim 3, wherein fatty acids having 18 and greater carbon numbers account for 70 to 85 wt. % of all the fatty acids in the combination of ingredients (A) and (B).

16. The cleansing composition of claim 3, where the weight ratio of ingredient (A) to ingredient (B) is in a range of 0.1<(A)/[(A)+(B)]<0.9.

17. The cleansing composition of claim 4, wherein said surfactant is present in an amount of 1 to 70 wt. %.

18. The cleansing composition of claim 3, wherein a total content of ingredients (A) and (B) in said cleansing composition is 0.3 to 10 wt. %.

19. The cleansing composition of claim 3, wherein said cleaning composition has a pH of from 3 to 4.

20. The cleansing composition of claim 3, wherein a content of ingredient (A) or (B) in said aqueous liquid in which the ingredient (A) is suspended or in said aqueous liquid which contains said molten ingredient (B) is 0.1 to 50 wt. %.

* * * * *